United States Patent [19]

Coggins

[11] 3,932,601

[45] Jan. 13, 1976

[54] METHOD AND COMPOSITION FOR THE DIAGNOSIS OF EQUINE INFECTIOUS ANEMIA VIRUS INFECTION BY USING AGAR-GEL-IMMUNODIFFUSION REACTION

[75] Inventor: Leroy Coggins, Ithaca, N.Y.

[73] Assignee: Cornell Research Foundation, Inc., Ithaca, N.Y.

[22] Filed: Nov. 5, 1971

[21] Appl. No.: 196,060

Related U.S. Application Data

[63] Continuation-in-part of Ser. No. 132,073, April 7, 1971, abandoned.

[52] U.S. Cl.................................... 424/12; 424/89
[51] Int. Cl.[2] ................. A61K 39/12; G01N 31/00; G01N 33/16
[58] Field of Search............................. 424/12, 89

[56] References Cited
OTHER PUBLICATIONS

Saxer, Schw. Arch. Fitier., Vol. 108, 1966, pp. 331–334.
Saxer, Path. Microbiol. Vol. 23, 1960, pp. 722–726.
Lennette, Diag. Proc. for Viral & Rickett Dis. Am. Pub. Health Asso., 3rd. Ed., 1964, pp. 13–21, 28–32, 714.
Norcross & Coggins, Infection & Immunity, Vol. 4, Nov. 1971, pp. 528–531.

Coggins & Norcross, The Cornell Vet., Vol. LX, No. 2, Apr. 1970, pp. 330–335.
Saxer, Schweizer Archiv. fur Tierheilkunde, Vol. 102, 1960, pp. 232–254.
Coggins et al., The Vet., Bull., Vol. 41, Jan. 1971, p. 22, No. 150, (citing, Cornell Vet., 1960, 1970, 330–335).
Nakajima, Arch. Gesamte Virusforch, 28:348–360, (1969).
Moreman et al., The Southwestern Vet., Spring, 1966, pp. 183–186.

*Primary Examiner*—Sam Rosen
*Assistant Examiner*—A. P. Fagelson
*Attorney, Agent, or Firm*—Jones, Tullar & Cooper

[57] ABSTRACT

Method and composition for the diagnosis of equine infectious anemia virus infection in animals involving the use of an immunodiffusion reaction plate, wherein separate wells in the reaction plate contains an antigen associated with the virus, an antiserum to the virus and the serum of the suspect animal. A positive response is indicated by a precipitin line of identity between the antigen well, antiserum well and the suspect serum well. Also disclosed is a novel antigen composition and a method for obtaining the same which is particularly suited in a diagnostic test for equine infectious anemia in animals.

6 Claims, 6 Drawing Figures

METHOD AND COMPOSITION FOR THE DIAGNOSIS OF EQUINE INFECTIOUS ANEMIA VIRUS INFECTION BY USING AGAR-GEL-IMMUNODIFFUSION REACTION

This application is a continuation-in-part of my copending application Ser. No. 132,073, filed Apr. 7, 1971 now abandoned.

The present invention relates to a novel antigen preparation produced as a result of an infection with the virus, a method of obtaining the same, and an improved test for diagnosing equine infectious anemia with improved accuracy, rapidity and simplicity.

BACKGROUND OF THE INVENTION

Equine infectious anemia (EIA), commonly known as "swamp fever," is a disease which primarily affects horses and ponies. The disease is world wide in distribution and has been extensively investigated for many years to elucidate the morphological and physicochemical properties of the virus, to develop a satifactory diagnostic test for the virus, to find a possible vaccine and to study the epideminology and spread of the infection.

One of the major problems associated with equine infectious anemia is that until recently little or no antibody response could be detected. Recently, researchers have described complement-fixing and neutralizing-antibody responses to this virus, as well as a procedure for purification and concentration of the virus, (Nakajima et al., *Arch. Gesamte Virusforsch* 28: 348 – 360 (1969).

Despite the advances made in connection with describing some of the characteristics of the virus, a development of a satisfactory diagnostic test for EIA has defied the efforts of many of the prior art workers. Practically all conceivable tests and technics have been attempted at one time or another, and until only very recently, no satisfactory means of assaying the virus or antibody has been available. The use of horse-leukocyte cultures in conjunction with the complement-fixation to assay the virus and antibody has been described (Kobayashi et al., *Nat. Inst. Anim. Health Quart.* 7: 8 – 20 (1967) and Kono et al., *Nat. Inst. Anim. Health Quart.* 7: 138 – 144 (1967) and the results appear to explain many of the unique features of the disease; however, the procedure has not been confirmed by other prior art workers.

As it is well known by prior art workers studying EIA, acute and chronic cases of EIA can often be recognized by the clinical symptoms exhibited. However, clinically recovered carriers without the aid of a good diagnostic test may escape the suspicion of even the most astute observer. For example, it has been described that chronically infected horses have been observed experimentally to appear healthy for many years and yet persistently maintain virulent EIA virus in their blood stream. As a result of the dilemma of being unable to ascertain whether an animal is chronically infected with EIA, disease control officials have been in the predicament of trying to prevent the spread of EIA. Thus, the detection of a carrier horse has required the use of the animal inoculation test which usually takes about 90 days and costs about $500.00.

The immunodiffusion reaction technique has been a useful diagnostic and analytical tool for several known diseases. The immunodiffusion reaction involves conducting a reaction between an antigen and an antibody. This reaction is generally effected in a semisolid media such as agar. Both reactants are initially soluble in the medium or carrier, i.e., they diffuse or permeate through the matrix material, but the reaction product (or complex) is insoluble therein and may be observed visually or photographically. A more detailed discussion regarding the immunodiffusion reaction may be found in "Immunodiffusion", by A. J. Crowle, Academic Press, New York, the disclosure of which is incorporated herein by reference.

The success of employing the immunodiffusion reaction technique as a diagnostic test is often dependent upon a relatively pure antigen, which is not substantially tied up or contaminated with antibodies to the antigen. Also, the presence of other contaminating materials will hamper the success of this technique. The titer of the antigen, therefore, must be relatively high in the immunodiffusion reaction technique in order to form a precipitin line of identity with the antiserum. Likewise, the titer of the antiserum must be sufficient so that the antigen and antiserum will form a precipitate. Until recently, antigen for EIA having a high enough titer to form a precipitin line with antiserum has not been available, and, accordingly the use of the immunodiffusion reaction has not been considered by the prior art workers an available tool in diagnosing EIA.

SUMMARY OF THE INVENTION

It is an object of the present invention to provide an accurate, inexpensive diagnostic test for presistent chronic virus infections.

It is another object of the present invention to provide an accurate, inexpensive diagnostic test for equine infectious anemia (EIA).

It is still another object of the present invention to determine prior exposure to equine infectious anemia virus and susceptibility to the virus.

It is still a further object of the present invention to prepare a novel equine infectious anemia antigen preparation in a form which is suitable for use in an immunodiffusion reaction.

These and other objects are obtained by conducting an antigen-antibody reaction by immunodiffusion wherein the antigen is obtained from an organ extract of an animal acutely infected with equine infectious anemia or concentrated leukocyte culture infected with equine infectious anemia virus.

The invention will appear more clearly from the following detailed description when taken in connection with the accompanying drawings, by way of example, a preferred embodiment of the inventive idea.

DESCRIPTION OF THE PREFERRED EMBODIMENTS

Figure 1:
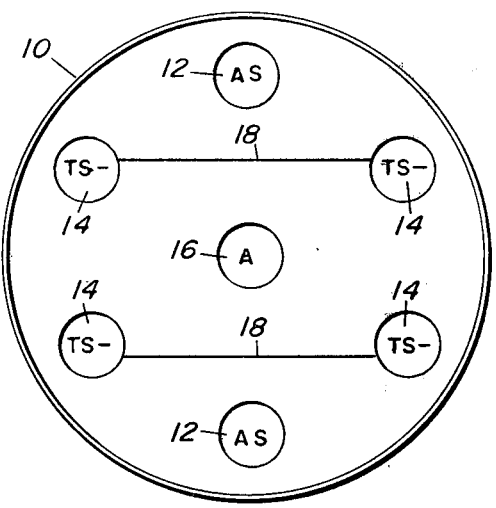
FIG. 1 illustrates an immunodiffusion reaction on a test plate of agar with six wells, wherein two wells contain reference antiserum to EIA (AS) and four wells contain test serum(TS$^-$) from an animal not infected with EIA virus, all of which surround a central well containing EIA antigen (A).

The immunodiffusion test for EIA used in accordance with the practice of the present invention detects the precipitating antibody specific for the disease of EIA. The test is conducted by cutting wells in a layer of agar in a petri dish. Preferably, six wells 7 mm in diameter are spaced 3 mm apart around a central reservoir of the same diameter containing the EIA antigen. A reference serum that reacts with the EIA antigen to form a distinct precipitin line is placed in two opposite peripheral wells. The four remaining wells contain the suspect serums. Such an arrangement facilitates an accurate determination of lines of identity, i.e., the coalescence of the suspect precipitin line with the control line.

PREPARATION OF ANTIGEN

The antigen to be used in the practice of the present invention may be extracted from the spleen or other organs of an animal, such as a horse or pony, which is acutely infected with equine infectious anemia. The antigen may also be obtained from infected tissue culture such as horse leukocyte culture and concentrated for use in the immunodiffusion test. The preparation of the purified concentrate is described by Nakajima et al., *Arch. Gesamte Virusforsche*, 28, 348 – 360 (1969), the disclosure of which is incorporated herein by reference.

Preferably, the antigen is obtained from an organ of an animal which has exhibited an immediate and severe febrile reaction following inoculation with a virulent virus of any of the several virulent isolates of EIA virus. The antigen is extracted from an organ of the animal after the animal has become febrile, i.e., about 9 – 11 days after inoculation with virulent EIA virus. Antigens obtained in this manner have a remarkably high sensitivity in the agar-gel-immunodiffusion reaction, i.e., a reaction occurs between the antigen and the serum of a diseased suspect animal.

The novel EIA antigen preparation of the present invention which have a high antigen concentration are preferably produced by inoculating an animal, preferably a pony or a horse, intravenously with from about 1 to about 300 ml. of serum infected with EIA virus. The larger volumes of infective serum, i.e., from 10 to 100 ml. sometimes produce shorter incubation periods. It has been found that a subinoculation of acute stage blood in an amount of about 300 ml. has helped to shorten the incubation period and cause a more severe illness.

The virus contained in the serum employed to inoculate the animal should be of sufficient titered virulence to cause a quick or rapid and severe febrile reaction in the animal in which one harvests the antigen, i.e., a fever of about 4° to 6° above normal. It has been found that serum containing titers of virulent virus of about $10^6$ to about $10^7$ animal infectious doses per ml. will produce the desired quick or rapid and severe febrile reaction.

In the event the inoculum strain isolate serum does not have titers of $10^6$ or $10^7$ animal infectious doses per ml., the titer can be increased by known techniques. For example, the weakly infected serum may be injected into another animal first, to infect the animal and allow the infectivity to increase. Usually the desired titers can be achieved by taking the serum from the animal about nine days after inoculation with the original weakly infectious serum having a low titer. Of course, other known methods of raising the titer may also be employed, such as harvesting the virus in tissue culture medium and concentrating.

The serum containing the EIA virus used as the inoculum can be obtained from any strains having the virulent EIA disease. Illustrative strains include the Wyoming strain, the German strain, the Goshun strain, the P337 strain, the Texas strain, the New York State strain, the New Jersey strain, etc.

It has been found that infected spleen extracts have a very high concentration of antigen, therefore, it is a preferred embodiment of the present invention to use the extract of spleen from the acutely infected animal as the source of antigen.

Ideally, the antigen is collected from the organ sterily, stored and frozen at minus 20°C. and thawed and frozen several times before using. Aging the infected and antigen containing organ in the freezer also appears to aid in the release of the antigen. Of course, other known extraction methods for releasing the antigen from the tissue of the organ may be employed, such as using ultrasonic sound, homogenization, acetone-ether extraction, etc.

If the antigens become diluted beyond 1:2 to about 1:4, their effectiveness generally is lost, however, it is possible to concentrate the antigen by precipitation with half-saturated ammonium sulfate and reconstitution in a smaller volume.

It is believed that the dilution factors described above frequently occur because the infected organs (especially the spleen) become engorged with large volumes of blood during and shortly after the animal becomes febrile from the EIA virus infection. Owing to the large volume of blood present, the recoverable antigen from the cells of the infected organ is diluted.

Rather than concentrating the antigen as described above, it has now been found that an EIA antigen preparation having a higher titer than previously obtained by the foregoing methods can be obtained by removing a substantial portion of the blood in the infected organ of the animal prior to extraction of the EIA antigen from the organ cells containing the antigen.

According to this embodiment of the present invention, the blood may be removed from the organ by any one of the several techniques known in the art.

For example, the organ, e.g., spleen, may be physically treated such as by squeezing or pressing to eliminate the blood prior to extraction.

Another technique comprises subjecting the organ cells containing EIA antigen to trypsination followed by centrifugation of the substantially plasma free cells.

A preferred technique for removing blood from the organs is to inoculate the diseased animal with a vasoconstrictor drug or a drug which causes the animal to release vasoconstrictors just prior to euthansia of the animal. This technique is preferably accomplished by inoculating the animal with an excess over the normal therapeutic dosage of the drug to obtain a quick response. A response is generally indicated by an increase in pulse and profuse sweating by the animal shortly after incoulation with the drug (usually within a few minutes after inoculation depending on the drug, etc.). When the animal has responded to the drug inoculation it is immediately sacrificed by shooting in the head and bled from the neck vessels. After the animal has been bled, the desired organ is taken from the animal by sterile techniques and frozen at minus 20°C. until used. By using the vasoconstrictor drugs or drugs which cause a release of vasoconstrictors in vivo, resulting in a constriction of the blood vessels, a large amount of the blood stored in the organs of the animal is temporarily displaced. Thus, by killing the animal and thereafter bleeding it shortly after the drug has taken affect, one may obtain an infected organ devoid of a substantial amount of the blood previously encountered in the infected organ. This technique, therefore, permits the subsequent extraction of the antigen preparation having a high titer without being diluted with a large quantity of blood. Also, the possibility of losing potent antigens during the process of removing blood from the infected organ extract is minimized by this technique.

Among the preferred vasoconstrictors suitable in the practice of the present invention include the compounds, 3,4-dihydroxy-α-[(methylamino)methyl]benzylalcohol, otherwise known as epinephrine, succinyl choline, and many other known compounds which will cause a shrinkage or constriction of the blood vessels in the infected organs of the infected animal.

It will be understood by those skilled in the art that the time of harvesting the EIA antigen in the animal after inoculation with the virulent EIA virus will vary depending on the health of the animal, the strength of the inoculum and many other factors. Generally speaking, the antigen will be at a high enough titer for use in the diagnostic test of the present invention a few days after the animal shows a severe febrile reaction from the EIA virus inoculation. Of course, if the animal is given a drug to reduce the fever, it is not necessary that a severe febrile reaction occur, and, accordingly, the antigen can be harvested up to the second week after the inoculation and still have a very high titer adequate for use in the diagnostic test of the present invention.

As it is well known in the art, the presence of antigen in the infected organ bring about the production of antibodies to the antigen. These antibodies, when present in large quantities will have a dilitory effect on the usefulness of the antigen in the diagnostic test of the present invention. Therefore, it is important that the infected organ be taken from the animal before a large amount of the antibodies are formed. Methods for determining the presence of these antibodies are known in the art, and the animal can be tested periodically during the inoculation period to ascertain their presence.

In the event the animal becomes moribund during the second week after inoculation with the virulent EIA virus, the organ should be taken from the animal as soon thereafter as possible. However, some healthy animals may not become moribund until about the third week after inoculation which is generally sufficient time for a large amount of antibodies to form. Therefore, it is most desirable to take the infected organ from the animal before these antibodies form in great quantities which is generally a short time after the animal has reached a peracute condition. In other words, the infected organ should be taken from the animal within a week after the animal has shown a fast and severe illness. With most horses and ponies, the ideal antigen formation without the presence of a substantial amount of antibodies occurs about 7 to 12 days after inoculation.

PREPARATION OF ANTISERUM

A positive reference antiserum can be chosen from an animal surviving EIA infection. Long term carriers often have been found to have satisfactory serums. The serums should give only one dense, distinct precipitin line when tested with the EIA antigen and the line should form approximately mid-way between the serum and antigen wells, with no tendency to broaden or fade with time. In the event the precipitin line is not mid-way between the antigen well and the antiserum well, the antiserum can be diluted or concentrated to achieve the desired concentration so that the precipitin line is equal distance between the antigen well and the antiserum well. The precipitin line should be shown to be specific by EIA horse infectivity test or by forming a line of identity with an antigen and an antiserum which has been shown to be specific for EIA by animal inoculation test. Serum with excess antibody in relation to antigen concentration tend to form a broad band rather than distinct line which is essential for accurate determination of line identity. It is much easier to see the suspect line coalesce with the reference line if the latter is a dense, narrow line. Discrete precipitin lines can be obtained with higher titer serums, but they must be diluted. Serums that give a non-specific cloudy ring around the well should be avoided. Thus, it is essential that the antiserum preparation be selected from a horse surviving EIA infection and one which gives only one dense precipitin line at a specific for EIA.

PREPARATION OF IMMUNODIFFUSION TEST PLATE

The immunodiffusion reactions for the present invention are preferably carried out in a 100 mm (outside diameter) plastic petri dish having therein a layer of agar in a procedure similar to that described in Coggins et al. *Am. J. Vet. Res.* 27, 485 – 488 (1966) for African Swine Fever. In order to prevent occasional seepage of serum underneath the agar, a base layer of 5 ml. of 2% Noble's special agar in a borate buffer can be used. When the base layer becomes hard a top layer of 12 – 15 ml. of 1% Noble's special agar in the same buffer can be added. The borate buffer is prepared by mixing 2 gm. of NaOH and 9 gm. of $H_3BO_3$ in a liter of distilled water. This buffer mixture should have a pH of about 8.6. Perservatives or sodium chloride need not be used. Since autoclave temperatures tend to cause some discoloration in the agar, the agar can be dissolved and melted by boiling. The agar can then be allowed to harden in the petri dishes at room temperatures with the lids partly open to allow moist air to escape. If excess water remains in the plate, it can cause dilution of the antigen. Best results are found with fresh plates, since the agar may become cloudy with age which may interfere with the interpretation of the test.

Of course, other materials known to those skilled in the art may be used in place of the preferred agar materials described above without departing from the scope of the invention.

A template with seven circular cutters can be used to cut six wells, 7 mm in diameter and spaced equidistance 3 mm apart, around a central reservoir of the same diameter. Four of the patterns are cut in each petri plate. Alternatively, a cork borer can be used to cut the wells as outlined on a paper underneath the petri dish or underneath a template. The cutters are preferably only allowed to cut through the 1% agar and the agar in the wells can be removed with a short pipette attached to a suction pump leaving the 2% agar base layer intact.

Figure 4:
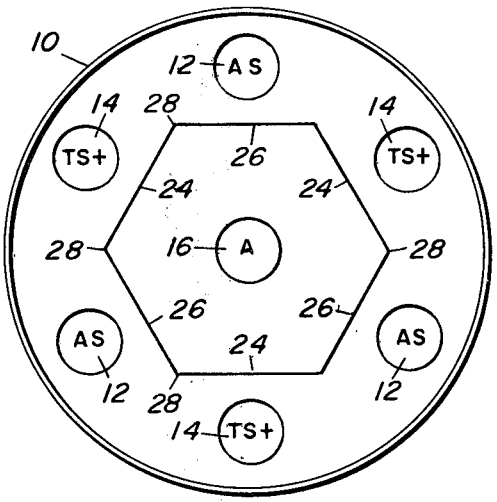
FIG. 4 illustrates an immunodiffusion reaction on a test plate of agar with six wells, wherein three wells contain reference antiserum to EIA virus (AS) and the three remaining outer wells contain test serum from an animal infected with EIA virus, all of which surround a central well containing EIA antigen (A).

The immunodiffusion reactions are preferably conducted by placing the antigen material (infectious splenic pulp or extract of such from horses infected with equine infectious anemai virus or concentrated leukocyte culture infected with EIA virus) in the central reservoir with special care in avoiding the formation of air pockets in the bottom of the well or over-filling the well. A positive reference serum can be placed in two wells on the periphery directly opposite each other and the four remaining wells were filled with suspect serum samples. For beginners the use of positive reference serum in three wells (i.e., every other outer well, as shown in FIG. 4) is suggested for greater ease in reading the test.

Referring to FIG. 1 in the drawings there is illustrated a test plate of agar 10 with 2 wells 12 containing reference antiserum (AS), four wells 14 containing test serum (TS⁻) from an animal not infected with EIA virus surrounding a central well 16 containing EIA antigen (A). The reference antiserum and antigen are from sources as from hereinabove described. Precipitin lines 18 illustrate the reaction product between the reference antiserum and antigen. The precipitin line is about equidistance between the antigen well and the antiserum wells and has a slight curvature toward reference antiserum well 12. The absence of precipitin lines between the test serum wells and the antigen well indicates that the serum is from an animal not infected with EIA virus.

Figure 2:
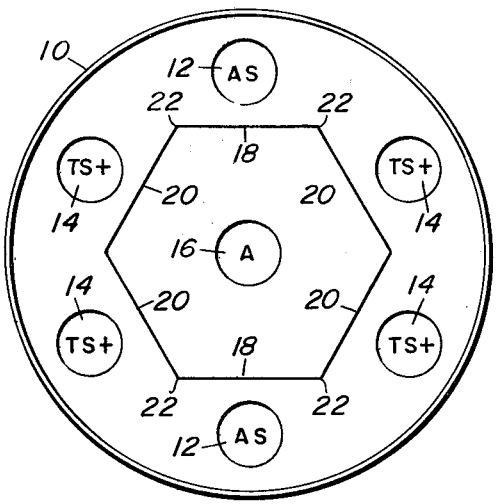
FIG. 2 illustrates the test plate of FIG. 1 except that the test serum (TS$^+$) is from an animal infected with EIA virus.

FIG. 2 illustrates a test plate as described above with reference to FIG. 1, except that wells 14 contain test serum from an animal infected with EIA virus. Equidistance between the antigen well (A) and test serum (TS⁺) wells there is formed a precipitin line of identity 20 which coalesce with the precipitin line 18 between the antiserum (AS) wells and the antigen at points 22. The schematic illustration in FIG. 2 is indicative that the test serum (TS⁺) is from an animal infected with EIA virus. In other words, the coalesced precipitin lines schematically shown in the drawing is the "precipitin line of identity" between the antigen well, the antiserum wells and the suspect wells. In some cases other lines appear because of the presence of other antigens in the antigen preparation in well (A) which react with antibodies in the test serum wells. However, these lines will not coalesce with the reference antiserum line at point 22.

Figure 3:
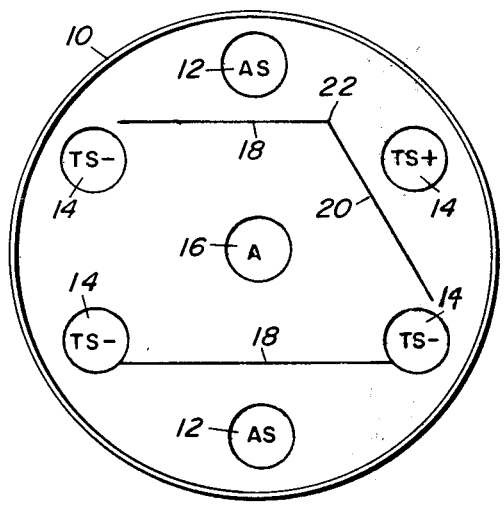
FIG. 3 illustrates still another test plate of FIG. 1 except that only one of the outer wells contain test serum from an animal infected with EIA virus, while the remaining three test serum wells (TS$^-$) contain serum from an animal not infected with EIA virus.

FIG. 3 illustrates another immunodiffusion reaction in a test plate similar to FIG. 1 except that only one of the outer wells 14 contain test serum from an animal infected with EIA virus, while the remaining test serum wells (TS⁻) 14 contain test serums from an animal not infected with EIA virus.

It can be seen from the illustration in FIG. 3 that a straight precipitin line 18 forms equidistance between the antigen well and the antiserum wells and a precipitin line 20 forms between the antigen well 16 and the test serum well 14. It can also be seen that lines 18 and 20 coalesce at point 22 to indicate that the serum from test serum (TS⁺) is from an animal infected with EIA virus whereas the serum from the remaining wells are from animals not infected with EIA virus. FIG. 3 further illustrates the flexibility of the diagnostic method of the present invention. In other words, it is possible that four separate horses can be tested on one immunodiffusion reaction test pattern while only using one sample of antigen and two samples of antiserum. Using four test patterns on a test petri plate, 16 horses can be tested.

FIG. 4 illustrates an immunodiffusion reaction on a test plate of agar containing six separate wells which surround a central well containing antigen preparation for EIA virus. The test plate in FIG. 4 is similar to FIGS. 1, 2 and 3 except that the antiserum and test serum wells are arranged differently and there are equal number of antiserum and test serum wells arranged alternatively. As it can be seen from the schematic illustration in FIG. 4, a precipitin line forms equidistance between each of the reference antiserum wells and the antigen well as well as precipitin lines equidistance between the test serum wells and the antigen well. Thus, the antibodies in the antiserum well migrate out in a circular pattern toward the antigen well and form a precipitin line 26. The test serum in the reaction illustrated in FIG. 4 is from an animal infected with EIA virus and therefore contains antibodies for EIA virus. This material also migrates in a circular pattern towards the antigen well to form a precipitin line 24, equidistance between the test serum wells and the antigen well. The illustration also reveals the coalescence between precipitin lines 24 and 26 at points 28, which is clearly indicative that the serum in wells 14 is from an animal infected with EIA virus. This reagent arrangement facilitates easy reading of weakly positive reactions as are shown in FIG. 5.

Figure 5:
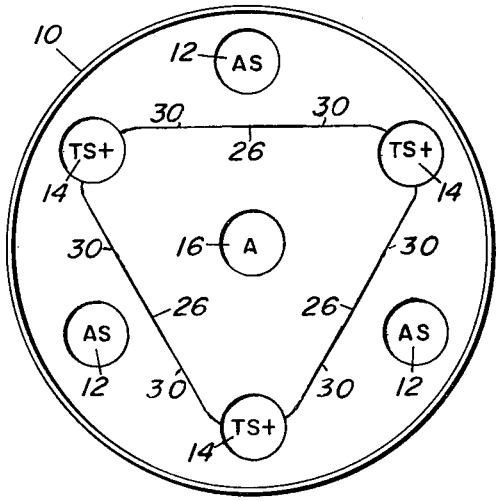
FIG. 5 illustrates the test plate of FIG. 4 wherein the test serum (TS$^+$) is from an animal infected with EIA virus, but having a low level of antibody.

FIG. 5 illustrates a test plate as described in FIG. 4 except that the test serum 14 is from an animal infected with EIA virus having low level of antibody in its serum. It can be seen that strong precipitin lines 26 form between the reference antiserum wells 12 and the antigen well 16. However, precipitin lines 30 only begin to form, but do not form a complete line between (TS⁺) well 14 and (A) well 16. As mentioned for FIG. 1, page 14, the reference control line has a slight curvature toward the reference serum. This curvature is helpful in detecting weak reactions which cause the reference line to turn in the opposite direction as in FIG. 5. Such reactions indicate the animal is infected with EIA virus.

Figure 6:
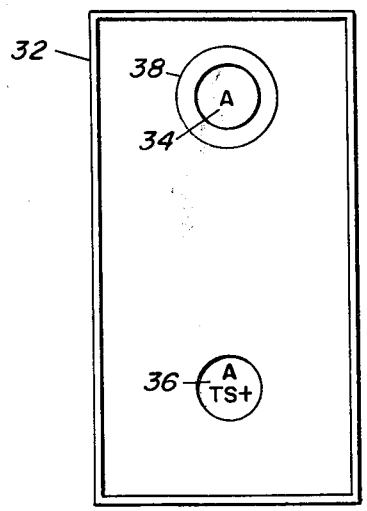
FIG. 6 illustrates an immunodiffusion reaction on a test plate which contains a uniform amount of antiserum to EIA virus in the agar test plate. The plate illustrated has two wells, one containing EIA antigen (A), either alone or with test serum from an animal not infected with EIA virus and the remaining well (A plus TS$^+$) contains EIA antigen and test serum from an animal infected with EIA virus. A halo is formed around the first well (A) but either does not form around the second well (A - TS$^+$) or is reduced in size.

FIG. 6 illustrates an immunodiffusion reaction on a test plate of agar 32, preferably on a slide rather than in a petri dish. This test plate of agar contains a uniform amount of antiserum to EIA virus. Well 34 contains EIA antigen preparation (A) and well 36 contains the same EIA antigen preparation previously mixed and incubated at 37°C. for 1 hour with an equal quantity of test serum from an animal infected with EIA virus. Since the antibodies in the serum from the infected animal immediately react with the antigen in well 36, no precipitin line or halo forms in the agar test plate. However, the absence of antibodies in well 34, permits the antigen preparation to migrate out of well 34 through the agar gel until the concentration of the antiserum and antigen are equal, wherein they form a precipitin halo 38. Well 34 may contain serum from an animal not infected with EIA virus mixed with the antigen preparation. If the animal does not contain antibodies to EIA virus, the antigen preparation migrates to form a precipitin line 38 as illustrated.

The agar gel employed in the tst plate described in FIG. 6 of the drawings can be formulated according to known immunodiffusion techniques, i.e., thoroughly mixing the antiserum in the agar and buffer. Preferably, a one percent Noble special agar in borate buffer is employed. For best results, the antiserum is diluted to a concentration which will give a weak reaction in the immunodiffusion reaction described in FIG. 1 of the drawings. Suitable dilutions for high titer antiserum for incorporation into the agar should be about 1 to 32 or more. Low titered antiserum are unsuitable because they cloud the agar. Of course, the use of a high titer antigen will permit the use of higher concentrations of antiserum.

As a modification of the technique described in FIG. 6, one may homogeneously mix a specified amount of antigen preparation in the gel-forming material, i.e., agar. According to this procedure the test serum is placed in either well 34 or 36, if there are two wells. However, by using this technique one well could suffice. If the animal is infected with EIA virus the antibodies in its test serum forms a precipitin circle 38 in the agar gel whereas serum from an animal not infected with EIA virus does not form any precipitin circle owing to the absence of antibodies specific to EIA virus. The use of this technique is particularly useful with the purified antigen extracts which are substantially free of any non-EIA antigens.

As a further modification of the foregoing technique of dissolving antigen preparation in the gel-forming material, it is possible to perform semi-quantitive analysis of EIA virus antibodies present in the serum of horses infected with EIA virus. According to this modification differing concentrations of antigen preparation are thoroughly mixed in a plurality of test plates. By comparing the immunological reaction with standarized antibodies to EIA, one may determine the relative concentration of EIA antobody, and possible infection of EIA virus in the animal at various stages of the sickness.

The following examples serve to more fully describe the manner of making and using the above-described invention as well as to set forth the best modes contemplated for carrying out various aspects of the invention. It is understood that these examples in no way serve to limit the true scope of this invention, but rather are presented for illustrative purposes only.

EXAMPLE 1

A susceptible pony was inoculated with the Wyoming isolate (described by Stein et al., Amer. Jour. Vet. Res., 3;183 (1942) of equine infectious anemia virus that had been cultivated in horse-leukocyte-tissue culture for 9 days. The animal became febrile at 5 days after inoculation (peak temperature 106°F.) and moribund at 10 days, at which time it was sacrificed. The spleen was frozen, thawed, minced finely, to be packed into agar wells.

Immunodiffusion reactions were carried out in 85 mm plastic plates containing 23 ml. of 1.5% Noble's special agar in a borate buffer (pH 8.6) and 1:1,000 merthiolate. Serum was used undiluted or serially diluted twofold. The splenic pulp teased from the connective tissue was packed in the central reservoir with the reference serum placed in two wells on the periphery directly opposite each other and the four remaining wells were filled with suspect serum samples. The plates were placed at room temperature (20°C.) and observed daily. Precipitin lines generally became visible after 24 hours but were more distinct at 48 to 72 hours. The plates were photographed unstained after 4 to 6 days.

Spleen from the pony reacted in the agar-gel-immunodiffusion test to form a precipitin line with serum collected from a pony that had survived repeated challenges with the Wyoming virus. The preinoculation serum gave no precipitin reaction.

To establish the validity of the foregoing observation and the specificity of the novel antigen, the following tests were made. Serum from the pony that survived inoculation with the Wyoming isolate was set up against spleens from two normal horses and one normal pony as well as against spleens taken from five additional ponies that showed clinical signs of equine infectious anemia within the 1 st week following artificial infection with the Wyoming stock virus. These spleens were collected 3 to 5 days after signs of EIA appeared. Precipitin reactions were seen with all five infected, but were not present with normal spleens. Spleen collected from a pony inoculated with a New York field isolate of equine infectious anemia virus which also gave a precipitin reaction with the Wyoming isolate antiserum indicated that a common antigen was possessed by the various isolates of equine infectious anemia virus. This fact was confirmed in adsorption tests in which infected spleen (Wyoming isolate) but not normal spleen removed the specific antibody after incubation for 1 hour at 37°C. from the Wyoming isolate antiserum as well as from serum of a pony that had survived infection with a Texas isolate of equine infectious anemia virus. Serum from guinea pigs hyperimmunized against equine abortion virus did not react against the EIA antigen.

Specificity of the antibody was determined by the following tests. Serums from 20 normal ponies contained no detectable antibody when tested in the agar-gel-immunodiffusion test nor did the preinoculation serums of a group of eight ponies. A majority of these serums contained neutralizing antibody against equine abortion virus. Following infection with EIA virus, the eight ponies developed antibody specific for EIA. An EIA hyperimmune serum used as a control to determine the line of identity in the immunodiffusion test did not form a precipitin line with equine abortion virus. Antibody was found in the serum of one field case; a horse with symptoms of recurring fever, anemia, loss of weight, and edema. A diagnosis of EIA in this case was confirmed by the inoculation of a susceptible pony with blood of the suspect horse. A line of identity formed in immunodiffusion reactions with serums collected from six ponies following infection with Wyoming isolate, one horse and one pony infected with the Texas isolate, and three ponies infected with three field isolates of EIA virus from New York State. Antibody appeared as early as 18 days after inoculation in one pony and was commonly found after 1 month. Stronger precipitin reactions were seen in later serum samples, especially from animals receiving repeated challenges of EIA virus. One pony has retained its antibody for two years after it last received an inoculation of EIA virus, wherein the pony was originally infected more than 3½ years ago.

In preliminary studies on extraction and fractionation, the EIA antigen was recovered from spleen by saline extraction followed by precipitation with half-saturated ammonium sulfate and dialysis against phosphate buffered saline, but some of the antigen was lost in the procedure. Antibody was recovered in the precipitate from serum treated with half-saturated ammonium sulfate and in the gamma-globulin fraction of antiserum fractionated by diethylaminoethyl cellulose column chromatography. A saline extract of infected spleen reacted with survivor serums to fix complement up to a titer of 1:40 in a complement-fixation test. Preinoculation serums from the same animals and saline extracts of normal horse spleen gave no complement-fixation reaction. Accordingly, results of the complement-fixation test have correlated well with results obtained in the immunodiffusion test.

Based upon the observations from the foregoing tests, it appears important to select animals that react severly within the 1st week after infection for preparation of the novel antigen of the present invention and to harvest the spleen after 3 to 5 days of high temperature. Antigens prepared from spleens taken later in the infection were found to be weak, perhaps because there is sufficient antibody already produced to mask the antigen. A strongly reacting antigen and antiserum included in each test have been helpful to ascertain the line of identity. Otherwise fuzzy lines and boundaries of cloudiness around the serum wells sometimes confuse accurate reading of the reaction patterns. Adsorption of serums with normal spleen has helped to sharpen the specific precipitin lines in some cases. It has also been important to provide a proper equivalent ratio of reactants; a condition which appears to be especially important with horse serum antibody. Thus, in some cases it has been necessary to make dilutions (1:2 to 1:4) of the antiserum to get clear, distinct precipitin lines, especially against the weaker antigen preparations. Freezing and thawing of the spleen aided in obtaining stronger reactions, probably as a result of rupturing the cells and releasing of the antigen.

The immunodiffusion reaction has been shown to be an accurate and reliable test for the detection of EIA infection in the horse except for animals in the early stages of infection and foals of infected dams. Since the test measures antibody produced as a result of EIA infection, horses in the first two to three weeks of infection and before antibody is produced will test negatively. Such animals should be bled again in a week or two. In order to make a diagnosis in a young foal it is necessary to determine the antibody status of the dam. If the mare is negative then her positive reaction foal can be declared infected. If the mare has EIA antibody then the foal may or may not be infected. Only a gradual decline and eventual loss of the antibody over a period of several months will indicate absence of infection. A few foals have maintained their maternal antibody for 4 and 5 months.

EXAMPLE II

The EIA antigen in this test was prepared by inoculating a pony with 1 ml. of serum containing virulent Wyoming isolate of EIA virus (titer approximately $10^7$ pony infectious doses per ml.). The pony became febrile at 7 days post inoculation and had a high temperature of 106°F. at 10 days post inoculation. Spleen was harvested from this animal at 11 days post inoculation and frozen and thawed several times before it was used. Serum collected from pony several months after infection with Wyoming EIA virus was used as the positive reference antiserum. This serum, when tested against EIA spleen antigen, produced one sharp, dense precipitin line that was specific for EIA. The immunodiffusion reactions were incubated at room temperature in a moist inverted beaker and observed daily over a strong narrow beam of light for precipitin bands. Visible lines were commonly seen at 25 hours but weak reactions became more distinct by 48 hours. Serums containing high titers of antibody (1:32 and 1:64) produced broad, diffuse precipitin bands situated near the antigen well. More distinct lines formed when diluted. Such serums were detected by the abrupt ending of the reference line halfway across its normal position and were confirmed as positive by making two-fold dilutions of the suspect serum. Low titered antiserums, which as were found in animals shortly after initial infection and in foals receiving maternal antibody, or at terminal dilutions of high titered antiserums, did not always form complete lines but sometimes caused only a slight deflection of the reference line toward the test serum well. These weak reactions were confirmed by setting them up in duplicate and using a positive reference serum on each side of the suspect well. Increasingly higher levels of antibody caused the precipitin line to form more centrally between the serum and antigen wells and, in general, were clearly observable at 24 hours.

Ponies of varying ages and weights from the surrounding areas of Ithaca, New York were used as experimental test animals. They were housed in individual isolation units. In the beginning ponies were tested for the presence of EIA virus by the cross-transfusion of whole blood among a group of three ponies and observed for a period of 60 days. When it became evident that the immunodiffusion test was a reliable indicator for determining prior exposure to EIA virus, each pony was then required to be serologically negative for at least one month prior to their being used in experiments. Body temperatures of the experimental ponies were recorded twice daily and packed cell volume, white blood cell and platelet counts, and differential white blood cell counts were performed on the blood of each animal 6 days a week. Serum was collected once a week and stored at minus 20°C.

A bank of pre- and postinoculation EIA serums had been accumulated at Cornell University from experimental EIA studies conducted over the preceeding years. An early project was to test these serums for correlation between the inoculation of EIA virus and subsequent antibody production. As it can be seen from Table 1, serums from a total of 188 ponies taken upon arrival were tested for EIA antibody and all were negative. This finding was in agreement with the failure of any of the cross-transfused ponies to show signs of EIA. Of the 111 ponies inoculated with EIA virus or blood collected from suspected field cases of EIA which produced typical symptoms in the pony, all developed EIA antibody about 1 month after inoculation. None of the 77 control animals inoculated with blood from normal horses or other agents such as piroplasmosis and equine abortion virus, developed EIA antibody. Two ponies which received blood from field cases which were suggestive of EIA developed EIA antibody but no clinical symptoms of the disease. Subinoculation of their blood into two additional ponies resulted in clinical EIA as well as EIA antibody production. In no case did EIA antibody disappear from an animal once it was formed. One clinically recovered pony has been normal for over 3 years and yet has retained its EIA antibody as well as EIA virus.

TABLE 1

| Detection of EIA Antibody in Experimental Ponies | |
|---|---|
| Serum | No. pos. / examined |
| Preinoculation | 0/188 |
| Post-EIA Infection | 111/111 |
| Controls* | 0/77 |

*Uninoculated or inoculated with an agent other than EIA.

EXAMPLE III

Antiserums prepared against both type of equine piroplasmosis,[a] equine arteritis virus,[b] equine abortion virus (Herpes I),[c] and African Horse Sickness (types I and II)[d] have given no cross-reactions with the EIA antigens. In addition EIA antiserum did not cross-react with equine abortion virus precipitin antigen. Antigens prepared from ponies infected with EIA viruses from Wyoming, New York and New Jersey isolates reacted similarly in the immunodiffusion test.

[a]Obtained from Dr. A. A. Holbrook, U.S.D.A., Beltsville, Md.
[b]Obtained from Dr. W. H. McCollum, University of Kentucky, Lexington, Ky.
[c]Obtained from Dr. L. E. Carmichael, Cornell University, Ithaca, N.Y.
[d]Obtained from Dr. J. J. Callis, PIADL, Greenport, N.Y.

The development of EIA antibody in infected ponies was examined. The data in Table II shows that 65% of the ponies produced specific antibody by 3 weeks post inoculation and that 88% had developed antibody by 4 weeks. Antibody responses were detected in all ponies by 45 days post inoculation. The seven ponies with late antibody responses also had delayed clinical responses. The earliest antibody was detected 14 days after inoculation.

EXAMPLE III

A sequential analysis formula was followed to test the hypothesis that the presence of EIA antibody in a horse also indicated the presence of EIA virus. Such a condition seemed likely because previous experimental studies have demonstrated the long term persistence of EIA virus in the horse. Several hundred horses from the states of New York, Virginia, New Jersey, Pennsylvania, and Delaware were screened for EIA antibody. These horses represented acute, chronic, and inapparent cases of EIA. Whole blood collected in heparin from 85 serologically positive horses was inoculated individually into test ponies. The results of the test are shown in Table III. Similarly blood from 78 negative horses was inoculated into ponies. Ten ml. of blood was inoculated intravenously except in a few cases in which a volume of 300 ml. was injected. Response of the pony was measured by increase in body temperature ($2°$ being considered a fever), a drop in packed cell volume, a decrease in platelet counts, development of EIA antibody, and histological lesions of EIA (mononuclear infiltration of liver, spleen, splenic lymph node, and heart) as necropsy. A clinical diagnosis of EIA was made in 83 ponies and 84 ponies developed EIA antibody indicating actual infection with EIA virus. In five cases the experimental ponies did not react to the first inoculation of blood and four of the five suspect horses were subsequently rebled. The fifth horse could not be resampled because it had been destroyed in the meantime. In all of these cases the original blood sample had been forwarded to the laboratory through the mail in an ice package and arrived in what appeared to be good condition. In resampling, however, care was taken to hand carry the blood to the laboratory in ice as quickly as possible (usually within 4 – 6 hours) and to inject it into a test pony immediately. In the four cases retested in this manner 10 ml. of blood was inoculated again into the original pony and a larger amount (300 ml.) was injected intravenously into a second pony. In the four cases all experimental ponies then produced EIA antibody and all but one developed clinical signs of EIA. Subinoculation of this subclinical case of EIA seems to indicate that this virus is a mild strain of EIA virus. Elevations of $1° - 2°$ Fahrenheit of temperature were noted after two passages in ponies and EIA antibody has been produced in each case. Thus, if one eliminates the single failure for the probable reason of inactivation of virus in transit, then virus was demonstrated in 84 out of 84 serologically positive horses. The results of the test are shown in Table III, below.

TABLE II

Development of EIA Antibody in Experimentally Infected Ponies

| Weeks Postinoculation | No. Ponies positive for first time | Cumulative number ponies positive | percent of total |
|---|---|---|---|
| 2 | 1 | 1 | 2 |
| 3 | 36 | 37 | 65 |
| 4 | 13 | 50 | 88 |
| 5 | 3 | 53 | 93 |
| over 5 | 4* | 57 | 100 |

*The longest time before antibody was detected was 45 days in one pony.

TABLE III

Correlation of Immunodiffusion Test and Pony Infectivity Test

| EIA antibody status of donors | Pony Infectivity Test (No. Positive) | | | | | |
|---|---|---|---|---|---|---|
| | Fever | Drop PCV | Drop in platelets | EIA antibody | Lesions | EIA infected/ total studied |
| Positive (85) | 83 | 80 | 64 | 84 | 78* | 84/85** |
| Negative (78) | 2 | 2 | 2 | 1 | 2 | 1/78+ |

*Only 78 animals were examined histologically.
**The single horse in which infective EIA virus was not demonstrated was destroyed before it could be retested and it is assumed that the EIA virus was inactive in transit to the laboratory.
+This single failure was due to a horse in the incubation stage of EIA infection.

EXAMPLE IV

Blood from 78 serologically negative horses was inoculated into ponies. Two of the inoculated ponies developed clinical symptoms indistinguishable from EIA but only one developed EIA antibody. In the clinically ill pony which remained serologically negative for EIA a diagnosis of equine piroplasmosis was made by complement fixation test and blood smears. The donor horse also remained serologically negative for EIA. The other serologically negative donor horse, whose blood infected a pony, became clinically ill with symptoms of EIA 10 days after blood was collected. Thus, it was suspected that this horse was in the incubative stage of EIA when first tested and it was expected that the test pony would become infected with EIA. A retest of this horse 2 weeks later revealed EIA antibody and EIA virus was again demonstrated in its blood by pony inoculation. Thus, if this one horse is eliminated from tabulation on the grounds of being in the incubation stage of EIA then no EIA virus was demonstrated in any of the 77 negative horses tested and it is concluded that there have been no failures with the immunodiffusion test for EIA as an indicator of EIA infection.

The statistical procedure followed in this study required that if a minimum of 58 horses, tested in sequence, were serologically negative in the immunodiffusion test and were, in fact, free of EIA virus as demonstrated by animal inoculation test and that if a minimum of 58 serologically positive horses were infected and still carrying EIA virus then the hypothesis that the immunodiffusion test is at least 95% accurate can be accepted with 95% confidence. The exact level of accuracy of a technique, such as the immunodiffusion test for antibody, could only be measured by testing an infinite number of horses; consequently, some uncertainty must always exist as to whether the technique actually satisfies the specific minimum requirement of 95% accuracy. A 5% level of uncertainty has been adopted in most scientific fields.

Since the horses tested did not represent a random sample from the existing and future horse population, there is always the possibility of encountering distinctive groups of animals, perhaps infected with another microorganism that shares antigen with EIA or a specific strain of EIA that does not have a common antigen with our test antigen, in which case the antibody test will fail. This possibility can be guarded against by maintaining periodic checks on the immunodiffusion test by horse infectivity tests after it has been put into practice. Then, too, the test will be no better than the technical competence of the operators and the accuracy of the interpretations of the line of identity. All new antigens and reference antiserums must be tested against a reference EIA precipitin line which has been shown to be specific for EIA.

In addition to being useful as a diagnostic test and as a means of determining susceptibility of test ponies to EIA virus, the EIA immunodiffusion test is a valuable tool for the study of the incidence of EIA in horses.

EXAMPLE V

Several susceptible horses were inoculated intravenously with 10 ml. of virulent high-titer EIA virus (Wyoming isolate). The horses became febrile within 7 days and had temperatures of at least 105°F. Nine days after inoculation with the virulent EIA virus, the horses were injected intravenously with 10 ml. of a 1:1000 solution of epinephrine. Three minutes after being injected with the epinephrine, the horses were sweating and showed signs of being affected by the vasoconstrictor drug. Upon noticing the horses reacting to the vasoconstrictor drug, (3 minutes after injection with epinephrine), the horses were sacrificed by shooting in the head and they were immediately bled from the neck vessels. The spleens of each of the horses were harvested by sterile techniques and frozen at minus 20°C. until used.

For use in the immunodiffusion test in accordance with the practice of the present invention, the spleens were thawed and frozen twice. The pulp of the spleens was scraped from the stroma and used undiluted or extracted as follows:

The recovery of the antigen from remaining pulp of the spleens was extracted in the following manner. For each 10 gm. of splenic pulp, 30 ml. of borate buffer at pH 8.6 (9 gm. of $H_3BO_3$ and 2 gm. NaOH in a liter of distilled water) was added and the mixture was homogenized at 23,000 r.p.m. for 3 minutes. Homogenizing flask was held in ice both during extraction operation. The suspension was then frozen, thawed, and centrifuged at 2,000 g. for 20 minutes. The supernatent which contained the EIA antigen was collected, dispensed in 10 ml. vials and lyophilized. The antigen was stored at 20°C. (room temperature) and was reconstituted with 10 ml. of sterile distilled water just prior to use. The stroma contained no antigen and was disgarded.

The antigen preparation from non-extracted, fresh-frozen spleen pulp, when used in the agar-gel-immunodiffusion test plate as shown in FIG. 2 formed two precipitin lines in the test for antigen activity. Heating the antigen at 37°C. for 2 hours destroyed the antigen responsible for the weak second line. The stronger EIA antigen was not affected by this treatment and formed a single well-defined line in the test.

By employing the method outlined above, which produces a highly potent antigen for EIA, it was calculated that spleen from one infected horse will provide sufficient antigen to test at least 50,000 horses. Accordingly, this technique allows efficient production of antigen preparations for widespread use in diagnosing equine infectious anemia virus in animals throughout the world.

While in the foregoing description, the embodiments of the present invention have been set forth, it will be understood by those skilled in the art that considerable variation may be made in such detail without departing from the spirit of the invention.

I claim:

1. A method for obtaining an antigen preparation of equine infectious anemia virus useful in the diagnosis of said virus infection in animals, said antigen preparation being specific in its reaction with equine infectious anemia virus antibody, which method comprises
    a. inoculating an equine with a virus of equine infectious anemia having sufficient virulence to render said equine severely febrile rapidly after being inoculated with said virus;
    b. removing the equine infectious anemia virus infected spleen from said equine shortly after said animal becomes febrile, but before the antigen in said spleen becomes substantially tied up or contaminated with antibodies to the antigen,
    c. forming a spleenic tissue pulp, causing release of an equine infectious anemia virus antigen from the spleenic pulp, thereby providing an extract comprising said antigen preparation.

2. The method of claim 1 where the antigen extracted from the spleenic pulp is subsequently concentrated.

3. The method of claim 1 where the equine is inoculated with the Wyoming strain of equine infectious anemia virus.

4. The method of claim 1 where the organ is taken from said equine from about 9 to about 11 days following inoculation with a virus of equine infectious anemia.

5. The antigen preparation prepared by the method of claim 1.

6. The method of claim 1 where prior to obtaining said antigen extract a substantial portion of the blood in the spleen is removed.

* * * * *